United States Patent [19]

Malpass et al.

[11] Patent Number: 4,707,462

[45] Date of Patent: Nov. 17, 1987

[54] ORGANOMAGNESIUM SOLUTIONS OF LOW VISCOSITY

[75] Inventors: Dennis B. Malpass, LaPorte; Loyd W. Fannin, Dickinson; Clark C. Crapo, Houston, all of Tex.; Kelly B. Triplett, Stamford, Conn.

[73] Assignee: Texas Alkyls, Inc., Westport, Conn.

[21] Appl. No.: 855,290

[22] Filed: Apr. 24, 1986

[51] Int. Cl.$^4$ ............................................. B01J 31/12
[52] U.S. Cl. .................................. 502/153; 502/155; 502/115; 260/665 R
[58] Field of Search ....................... 502/115, 153, 155; 260/665 R

[56] References Cited

U.S. PATENT DOCUMENTS

| | | | |
|---|---|---|---|
| 3,578,642 | 5/1971 | Mueller et al. | 502/155 X |
| 3,646,231 | 2/1972 | Kamienski et al. | 502/153 X |
| 3,801,558 | 4/1974 | Fletcher et al. | 502/115 X |
| 4,213,880 | 7/1980 | Knight et al. | 502/155 X |
| 4,304,684 | 12/1981 | Langer | 252/429 B |
| 4,335,229 | 6/1982 | Sakurai et al. | 502/115 X |
| 4,387,045 | 6/1983 | Sakurai et al. | 502/115 X |
| 4,496,661 | 1/1985 | Shipley | 502/115 |
| 4,547,477 | 10/1985 | Malpass et al. | 502/153 |

FOREIGN PATENT DOCUMENTS 44665 1/1982 European Pat. Off. .
86644 8/1983 European Pat. Off. .

Primary Examiner—Patrick P. Garvin
Attorney, Agent, or Firm—Joel G. Ackerman

[57] ABSTRACT

The viscosity of hydrocarbon solutions of dialkylmagnesium compounds is reduced by including as the viscosity reducing agent a nitrogen-containing compound which is a piperidine substituted with a hydrocarbyl group (preferably a $C_1$–$C_6$ alkyl, $C_6$–$C_9$ aryl or $C_5$–$C_6$ cycloalkyl group) at the 2-position and optionally further substituted, triethylamine, cyclohexylamine, dicyclohexylamine, or N-N-dimethylformamide, or a mixture of two or more of these nitrogen-containing compounds. The viscosity reducing agent may be used as such or in the form of a substance produced by reacting such a nitrogen-containing compound with magnesium or with a dialkylmagnesium compound. The viscosity reducing agent may be used alone, or in a mixture with an organoaluminum viscosity reducing agent.

12 Claims, No Drawings

ORGANOMAGNESIUM SOLUTIONS OF LOW VISCOSITY

Organomagnesium compounds are known to be useful in a wide variety of chemical reactions. As reagents, organomagnesium compounds are used for the reduction of ketones, the metalation of aromatic compounds, and the alkylation of metal halides or oxides. As catalysts, organomagnesium compounds are useful in the dimerization and polymerization of olefins, see British Pat. No. 1,251,177; the polymerization of epoxides, see U.S. Pat. No. 3,444,102; and the preparation of telomers, see U.S. Pat. No. 3,742,077. While they perform many of the functions performed by Grignard reagents, organomagnesium compounds, owing to differences in electronic and steric factors, are more reactive toward certain types of compounds. See also U.S. Pat. Nos. 3,646,231 and 3,822,219.

Some of the most useful organomagnesium compounds are dialkylmagnesium compounds. Although some are insoluble in hydrocarbon solvents, it has been shown that those containing branched-chain alkyl groups, cyclic alkyl groups, or straight-chain groups of five carbon atoms or more are indeed soluble. Examples include di-tert-butylmagnesium, di-sec-butylmagnesium, di-n-amylmagnesium, methylisobutylmagnesium, ethylisobutylmagnesium, di-n-hexylmagnesium, etc. In addition, certain combinations of straight-chain lower alkyl groups have also been found to be soluble—n-butylethylmagnesium, n-butylmethylmagnesium, and n-propylmethylmagnesium. Such compositions are disclosed, for instance, in U.S. Pat. Nos. 4,207,207 and 4,222,969.

Unfortunately, most of the resulting solutions are highly viscous. Exceptions are solutions of branched-chain dibutylmagnesium compounds such as di-sec-butylmagnesium or mixed dibutyl compounds such as n-butyl-sec-butyl magnesium. This detracts from the utility of the compounds since their viscosity renders them less reactive as reagents and catalysts and more difficult to handle and transfer. In addition, the viscosity of the solutions makes it difficult to prepare the compounds in a form free of halides and other undesirable solids. Following the procedures described in Glaze and Selman, *Journal of Organometallic Chemistry*, Vol. 5, p. 477, (1967), and W. N. Smith, *Journal of Organometallic Chemistry*, Vol. 64, p. 25 (1974), dialkylmagnesium compounds are conveniently prepared by reaction between metallic magnesium and the appropriate alkyl chloride in the desired hydrocarbon solvent. The by-product of this reaction is magnesium chloride, which is insoluble in hydrocarbons. Both the magnesium chloride and any unreacted magnesium metal, which is frequently used in excess, remain as solid matter suspended in a viscous liquid. The viscosity prevents an easy separation of the solution of from the solids, requiring instead centrifuging equipment or the like for a long period for the solids to settle.

A number of different substances have been found effective in reducing the viscosity of such normally viscous solutions of organomagnesium compounds. These substances include, for instance, organometallic compounds of gallium, indium, and lithium (U.S. Pat. No. 4,299,781); chloroaryl solvents (U.S. Pat. No. 3,264,360); organoaluminum compounds (U.S. Pat. No. 3,737,393); cyclopentadiene (U.S. Pat. No. 4,447,369); and certain hindered phenols and anilines (European Patent Application, Publication No. 155,686).

SUMMARY OF THE INVENTION

It has now been determined that certain nitrogen-containing compounds are effective viscosity-reducing agents for hydrocarbon solutions of dialkylmagnesium compounds.

This invention comprises a hydrocarbon solution of a dialkylmagnesium compound having reduced viscosity, which solution comprises:
(a) a hydrocarbon solvent;
(b) a dialkylmagnesium compound normally soluble in hydrocarbon solvents; and
(c) an effective viscosity reducing amount of a nitrogen containing compound which is
  (i) a piperidine substituted with a hydrocarbyl group at the 2-position and optionally further sustituted; triethylamine; cyclohexylamine; dicyclohexylamine; or N,N-dimethylformamide; or a mixture of two or more of said nitrogen-containing compounds; or
  (ii) a substance produced by reacting such a nitrogen-containing compound with magnesium or with a dialkylmagnesium compound; or
  (iii) a mixture of (i) or (ii) with an organoaluminum viscosity reducing agent.

DETAILED DESCRIPTION OF THE INVENTION

The present invention pertains to low viscosity solutions of organomagnesium compounds in hydrocarbon solvents.

The term "hydrocarbon solvent" is used to designate aliphatic, cycloaliphatic and aromatic hydrocarbons. Illustrative of aliphatic solvents are n-pentane, isopentane, n-hexane, n-heptane, n-octane, isooctane, pentamethylheptane, and gasoline and other petroleum fractions. Illustrative of cycloaliphatic solvents are cyclohexane, methylcyclohexane, methylcyclopentane, cycloheptane, and cyclooctane. Illustrative of aromatic solvents are benzene, toluene, xylenes, ethylbenzene, tetralin, and alpha-methylnaphthalene. Preferred solvents are those containing 5 to 20 carbon atoms, inclusive. More preferred are those containing 6 to 15 carbon atoms, inclusive. Particularly preferred solvents are those which have boiling points between about 69° C. and about 110° C.

The dialkylmagnesium compound is one which is normally soluble in such hydrocarbon solvents, but which also normally forms viscous solutions therein. Illustrative of such dialkylmagnesium compounds are certain mixed dialkylmagnesiums such as butylmethylmagnesium, butylethylmagnesium, butyloctylmagnesium, and dialkylmagnesium compounds in which the alkyl groups have 5 or more carbon atoms each, preferably 5 to 20 carbon atoms, and most preferably 5 to 12 carbon atoms such as di-n-amylmagnesium, diisoamylmagnesium, di-n-hexylmagnesium, and di-n-octylmagnesium. Also included in such dialkylmagnesium compounds are hydrocarbon soluble mixtures of two or more dialkylmagnesium compounds such as diisoamyl plus diethylmagnesium, or three-component mixtures such as butylethylmagnesium plus di-n-hexylmagnesium.

The concentration of the dialkylmagnesium or mixture of dialkylmagnesium compounds in the solvent is not critical, and may vary over a wide range. In general, however, compositions according to this invention will contain one or more dialkylmagnesium compounds in an amount of from about 5 to about 60 weight percent of the overall composition, preferably from about 10 to about 30 weight percent.

The agents which have been found effective according to this invention to reduce the viscosity of hydrocarbon solutions of dialkylmagnesium compounds are certain nitrogen-containing compounds. In particular, these compounds are:

piperidines substituted at the 2-position by a hydrocarbyl group and optionally further substituted;
triethylamine;
cyclohexylamine;
dicyclohexylamine; and
N,N-dimethylformamide.

The hydrocarbyl groups substituted on the 2- and/or other positions on the piperidine ring are generally $C_1$–$C_6$ alkyl, $C_6$–$C_9$ aryl or $C_5$–$C_6$ cycloalkyl groups. The term "alkyl" includes both straight and branched chain groups such as methyl, ethyl, n-propyl, isopropyl, and the four butyl groups. Alkyl groups having from 1 to 4 carbon atoms are preferred, with methyl being most preferred. Cycloalkyl groups include cyclopentyl and cyclohexyl. Among the aryl groups, phenyl is preferred; substituents may also be present on the phenyl ring. In general, this class of compounds can be reresented by the formula

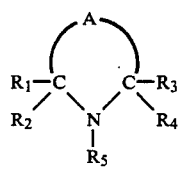

in which $R_1$–$R_5$ are independently hydrogen or a hydrocarbyl group as defined above, with at least one of $R_1$–$R_4$ being hydrocarbyl; and A is a trimethylene chain, optionally substituted.

In a preferred embodiment, $R_1$ is $C_1$–$C_6$ alkyl, $C_6$–$C_9$ aryl or $C_5$–$C_6$ cycloalkyl and $R_2$–$R_5$ are independently hydrogen, $C_1$–$C_6$ alkyl, $C_6$–$C_9$ aryl or $C_5$–$C_6$ cycloakyl.

More preferably, R is $C_1$–$C_4$ alkyl (most preferably methyl); phenyl or $C_5$–$C_6$ cycloakyl and $R_2$–$R_5$ are hydrogen, $C_1$–$C_4$ alkyl (most preferably methyl), phenyl or $C_5$–$C_6$ cycloalkyl. The trimethylene chain A is preferably unsubstituted but may be substituted on one or more carbon atoms by a hydrocarbyl, such as methyl or phenyl, or other functional group.

One class of such piperidines is those having a substituent on the nitrogen atom, that is, $R_5$ is a hydrocarbyl group as defined, preferably $C_1$–$C_4$ alkyl; most preferably methyl.

Another class is that in which $R_5$ is hydrogen.

In one subclass of such piperidines, $R_1$ and $R_3$ are both hydrocarbyl while $R_2$ and $R_4$ are hydrogen. Compounds of this type would have the formula

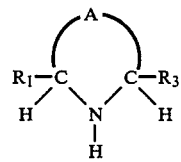

and include 2,6-di-(lower alkyl) piperidines, such as 2,6-dimethyl piperidines.

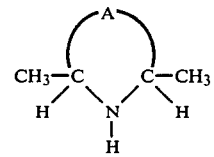

and 2,6-diphenyl piperidines

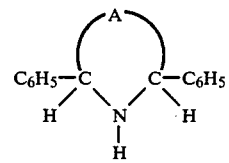

In another subclass of such compounds, $R_1$–$R_4$ are all hydrocarbyl, preferably all $C_1$–$C_4$ alkyl, most preferably methyl. Compounds of this last type have the general formula

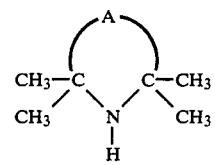

and include 2,2,6,6-tetramethyl piperidine.

Mixtures of two or more nitrogen-containing compounds as defined herein may also be used.

The viscosity reducing agents according to this invention may be introduced as such or in the form of a reaction product of the nitrogen-containing compound with magnesium or with a dialkylmagnesium compound and may be utilized alone or in combination with an organoaluminum viscosity reducing agent. Such substances are disclosed, for instance, in U.S. Pat. Nos. 3,737,393 and 4,127,507, and include: trialkylaluminum compounds such as trimethyl-, triethyl- and tri-n-hexylaluminum; mono- or dialkylaluminum halides such as diethylaluminum chloride or ethylaluminum dichloride; dialkylaluminum hydrides such as diisobutylaluminum hydride; aluminum alkoxides such as triisopropoxy aluminum; and aluminum halides, such as aluminum trichloride, which will react with the dialkylmagnesium, forming one or more of the above types of organoaluminum compounds. In such mixtures, the mole ratio of the nitrogen-containing compound to organoaluminum compound will preferably range form about 0.5:1 to about 2:1.

Particularly preferred for use in this invention is 2,2,6,6-tetramethylpiperidine, which has been found to be an especially effective viscosity reducing agent even when used alone. The use of this compound as the viscosity reducing agent will enable the preparation of hydrocarbon solutions of dialkylmagnesium compounds which, as opposed to most products on the market today, contain no added aluminum. Their use in polymerization processes therefore would not introduce additional and perhaps undesired amounts of aluminum into the reaction or process system. Inasmuch as 2,2,6,6-tetramethylpiperidine and other piperidines are known to be compatible with other components of a number of olefin polymerization catalysts, hydrocarbon solutions of dialkylmagnesium compounds which contain such piperidines are eminently suitable for use as starting materials for preparation of such catalyst compositions.

The invention is further illustrated by the following examples.

Nitrogen-containing compounds according to the invention were tested for reduction of viscosity of a composition containing n-heptane/n-butylethylmagnesium and magnesium chloride, resulting from the production of n-butylethylmagnesium by reaction of magnesium powder with n-butyl and ethyl chlorides. The viscosity of the n-heptane solution of n-butylethylmagnesium was measured at 35° C. Nitrogen-containing compounds tested for viscosity reduction were added to the n-heptane/n-butylethylmagnesium (BEM) slurry. The slurry was heated to 60° C. with stirring under a nitrogen blanket, then allowed to settle at ambient temperature. Viscosities were measured with an Ostwald viscosimeter at 35° C. The results are contained in the following table.

| Test Compound | % BEM Concentration | Mg/Test Cpd. mole ratio | Viscosity, cp at 35° C. | |
|---|---|---|---|---|
| | | | Without Test Cpd. | With Test Cpd. |
| 2-methylpiperidine | 9.8 | 35 | 1877 | 1144 |
| 2,6-dimethylpiperidine | 9.8 | 35 | 1877 | 162 |
| 2,2,6,6-tetramethylpiperidine | 10.5 | 49 | ca. 1000 | 10 |
| 2,2,6,6-tetramethylpiperidine | 9.8 | 88 | 1877 | 14 |
| cyclohexylamine | 9.7 | 7 | 682 | 276 |
| dicyclohexylamine | 9.8 | 71 | 1877 | 618 |
| N,N—dimethylformamide | 9.8 | 25 | 1343 | 127 |
| triethylamine | 9.8 | 59 | 1877 | 170 |

The amount of nitrogen-containing compound utilized is that which is sufficient to produce an effective reduction in viscosity. This amount will vary according to which nitrogen-containing compound is employed. In general, the mole ratio of magnesium to the nitrogen-containing compound will be between about 7:1 and about 100:1 or, inversely, the nitrogen-containing compound will be used in an amount of between about 1 and about 14 mole percent, with respect to the magnesium.

Of course, those nitrogen-containing compounds which can provide the greatest viscosity reducing effect when used in the smallest quantity are the most preferred.

What is claimed is:

1. A hydrocarbon solution of a dialkylmagnesium compound having reduced viscosity, which solution comprises:
   (a) a hydrocarbon solvent;
   (b) a dialkylmagnesium compound normally soluble in hydrocarbon solvents; and
   (c) an effective viscosity-reducing amount of a nitrogen-containing compound which is;
      (i) cyclohexylamine; dicyclohexylamine; or a piperidine having the formula

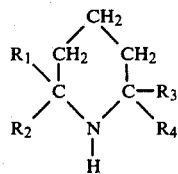

in which $R_1$–$R_4$ are independently hydrogen or a hydrocarbyl group selected from $C_1$–$C_4$ alkyl, $C_5$–$C_6$ cycloalkyl, and phenyl, at least one of $R_1$–$R_4$ being a hydrocarbyl group; or a mixture of two or more of said nitrogen-containing compounds;
      (ii) a substance produced by reacting such nitrogen-containing compound with magnesium or with a dialkylmagnesium compound; or
      (iii) a mixture of (i) or (ii) with an organoaluminum viscosity-reducing agent.

2. A hydrocarbon solution according to claim 1 in which the nitrogen-containing compound is of the type (i).

3. A hydrocarbon solution according to claim 2 in which the hydrocarbyl group is methyl.

4. A hydrocarbon solution according to claim 2 in which (i) is a compound having the formula

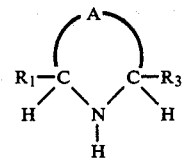

in which $R_1$ and $R_3$ are independently $C_1$–$C_4$ alkyl, $C_5$–$C_6$ cycloalkyl or phenyl.

5. A hydrocarbon solution according to claim 4 in which $R_1$ and $R_3$ are both phenyl.

6. A hydrocarbon solution according to claim 2 in which the nitrogen containing compound is 2-methylpiperidine.

7. A hydrocarbon solution according to claim 2 in which the nitrogen-containing compound is 2,6-dimethylpiperidine.

8. A hydrocarbon solution according to claim 2 in which the nitrogen-containing compound is 2,2,6,6-tetramethylpiperidine.

9. A hydrocarbon solution according to claim 1 in which the hydrocarbon solvent contains from 5–20 carbon atoms, inclusive.

10. A hydrocarbon solution according to claim 1 in which the dialkylmagnesium compound is n-butylethylmagnesium.

11. A hydrocarbon solution according to claim 1 in which the mole ratio of magnesium to nitrogen-containing compound is between about 7:1 and about 100:1.

12. A hydrocarbon solution according to claim 2 in which (i) is a compound having the formula

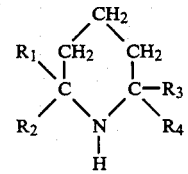

in which $R_1$–$R_4$ are all $C_1$–$C_4$ alkyl.

* * * * *